United States Patent
Leussler et al.

(10) Patent No.: US 11,896,359 B2
(45) Date of Patent: Feb. 13, 2024

(54) MULTI-CHANNEL MAGNETIC RESONANCE IMAGING RF COIL

(71) Applicant: KONINKLIJKE PHILIPS N.V., Eindhoven (NL)

(72) Inventors: Christoph Leussler, Norderstedt (DE); Ingo Schmale, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 869 days.

(21) Appl. No.: 16/962,244

(22) PCT Filed: Jan. 15, 2019

(86) PCT No.: PCT/EP2019/050859
§ 371 (c)(1),
(2) Date: Jul. 15, 2020

(87) PCT Pub. No.: WO2019/141645
PCT Pub. Date: Jul. 25, 2019

(65) Prior Publication Data
US 2021/0059556 A1   Mar. 4, 2021

(30) Foreign Application Priority Data
Jan. 18, 2018   (EP) ..................... 18152379

(51) Int. Cl.
*G01R 33/34* (2006.01)
*A61B 5/055* (2006.01)
*G01R 33/36* (2006.01)
*G01R 33/565* (2006.01)

(52) U.S. Cl.
CPC ........ *A61B 5/055* (2013.01); *G01R 33/34076* (2013.01); *G01R 33/3607* (2013.01); *G01R 33/3678* (2013.01); *G01R 33/5659* (2013.01)

(58) Field of Classification Search
CPC .............. A61B 5/055; G01R 33/34076; G01R 33/3607; G01R 33/3678; G01R 33/5659
See application file for complete search history.

(56) References Cited

U.S. PATENT DOCUMENTS

| | | |
|---|---|---|
| 4,857,849 A | 8/1989 | Sakamoto |
| 5,053,711 A | 10/1991 | Hayes et al. |
| 6,411,090 B1 | 6/2002 | Boskamp |
| 9,733,324 B2 | 8/2017 | Findeklee et al. |

(Continued)

OTHER PUBLICATIONS

International Search Report and Written Opinion from PCT/EP2019/050859 dated Apr. 18, 2019.

*Primary Examiner* — G. M. A Hyder (57) ABSTRACT

The present disclosure relates to a multi-channel magnetic resonance imaging RF coil (114) with at least four channels and comprising a coil element for each of the channels, the RF coil (114) further comprising for each coil element a socket (300-306) that is electrically coupled to said coil element via a respective first transmission line (209), each socket (300-306) being adapted for receiving a plug for providing an RF signal via the respective first transmission line (209) to the respective coil element, wherein with respect to a predefined RF signal the differences in electrical length between any of the transmission lines is $k\lambda/4$ where $k$ is an integer and $\lambda$ is the wavelength of the RF signal.

20 Claims, 4 Drawing Sheets

(56) References Cited

U.S. PATENT DOCUMENTS

| | | | |
|---|---|---|---|
| 2002/0169374 A1* | 11/2002 | Jevtic | G01R 33/365 600/422 |
| 2007/0016969 A1 | 1/2007 | Tu et al. | |
| 2009/0192382 A1 | 7/2009 | Nistler et al. | |
| 2011/0148418 A1 | 6/2011 | Findeklkee | |
| 2013/0134979 A1 | 5/2013 | McDougall et al. | |
| 2013/0300411 A1 | 11/2013 | Wiggins | |
| 2014/0307764 A1 | 10/2014 | Adolf et al. | |
| 2014/0375319 A1 | 12/2014 | Matschl | |
| 2015/0054506 A1 | 2/2015 | Eberler et al. | |
| 2016/0095552 A1 | 4/2016 | Ha et al. | |
| 2016/0238678 A1 | 8/2016 | Eberler et al. | |
| 2017/0016969 A1 | 1/2017 | Eberler et al. | |
| 2018/0081004 A1* | 3/2018 | Yang | H03F 3/2175 |

\* cited by examiner

MULTI-CHANNEL MAGNETIC RESONANCE IMAGING RF COIL

CROSS REFERENCE TO RELATED APPLICATIONS

This application is a U.S. national phase application of International Application No. PCT/EP2019/050859 filed on Jan. 15, 2019, which claims the benefit of EP Application Serial No. 18152379.6 filed on Jan. 18, 2018 and is incorporated herein by reference.

FIELD OF THE INVENTION

The invention relates to a multi-channel magnetic resonance imaging RF coil, a magnetic resonance imaging system for acquiring magnetic resonance data and a method of servicing a magnetic resonance imaging system for acquiring magnetic resonance data.

BACKGROUND OF THE INVENTION

Magnetic resonance imaging (MRI) is state of the art imaging technology which allows cross-sectional viewing of objects like the human body with unprecedented tissue contrast. MRI is based on the principles of nuclear magnetic resonance, a spectroscopic technique used by scientists to obtain microscopic chemical and physical information about molecules. The basis of both, nuclear magnetic resonance and MRI is the fact, that atomic nuclei with non-zero spin have a magnetic moment. In medical imaging, for example nuclei of hydrogen atoms are studied since they are present in the body in high concentrations like for example water. The nuclear spin of elementary particles can resonate at a resonant frequency, if a strong DC magnetic field is applied. This magnet resonance (MR) frequency is determined by the level of magnetic flux. In the MRI scanner, the magnetic field matches the selected resonance frequency only at a position in space. Only at this position the presence of these particles can be detected. By varying this position, an image can be measured.

The needed strong DC magnetic field (B0 field) is typically generated by superconducting magnets. In order to vary this field, such that it matches a given radio-frequency only at one position, a field gradient is generated using gradient coils. A field gradient can vary over time to achieve a scan.

To excite nuclear resonances, the RF coil generates a high frequency magnetic field at the nuclear resonance. The magnetic field must direct in a radial direction with respect to the axis of the MRI scanner. To achieve a radial magnetic field in all directions, a rotating field is used, which points in any radial direction at one point of time during one period. This is achieved using for example a so called 'birdcage' arrangement. Currents in opposing slabs of the birdcage flow in opposite direction and thus generate a radial field. Currents in neighbor slabs have a phase shift, such that the field rotates.

The coil is generally a highly resonant antenna, designed for generating the well-defined magnetic field inside the human body. As a side effect, electric fields are causing losses which strongly change the input impedance of the coil. This mainly affects the real part of the impedance, the relative change being linked to the resonance quality factor change, also called the load factor. This is typically in the range of 3-5 for today's birdcage resonators which are the preferred implementation for MRI body coils.

The power fed into the body coil is produced by pulse-mode amplifiers, which demand a good or at least acceptable power matching at their output. Conventional birdcage resonators are directly fed at the coil ports using matching circuits. At 1.5 T in quadrature operation, this is typically realized by using a hybrid coupler to drive two quadrature channels of the coil simultaneously. This coupler is a 4-port, which has the coil feeding ports connected to its outputs, the amplifier at one input and a load, typically 50 ohm, matching the transmission line impedance, connected to the fourth.

At 3 T, the two separate individually transmit channels may be connected via a transmit-receive box to the RF input ports of the body coil.

US 2017/0016969 A1 relates to a body coil that is provided with a quadrature drive.

SUMMARY OF THE INVENTION

Embodiments of the invention provide for a multi-channel magnetic resonance imaging RF coil comprising at least four channels and comprising a coil element for each of the channels, the RF coil further comprising for each coil element a socket that is electrically coupled to said coil element via a respective first transmission line, each socket being adapted for receiving a plug for receiving from the outside an RF signal that then is provided via the respective first transmission line to the respective coil element, wherein with respect to a predefined RF signal the differences in electrical length between any of the first transmission lines is $k\lambda/4$ where k is an integer and $\lambda$ is the wavelength of the RF signal The term 'coil element' refers to an arrangement of electrical conductors for converting an electrical current into a magnetic field. Thus, a coil element is the basic signal-generating component of a coil or coil array. To make the complex sensitivities of these coil elements sufficiently distinct for spatial encoding, the individual coil elements should be free of magnetic interactions.

The term 'channel' refers to the pathway of RF signal provided from an (external) RF source to the coil.

The term 'RF source' may refer to the component in the MRI system that provides the RF signal with desired amplitude and phase directly via a cable to the coil. For example, the RF source may be the output of an individual RF amplifier. Further, it may be the output of a splitter like a quadrature hybrid. A quadrature hybrid typically has an input connected to an RF amplifier and two outputs providing the signal of the RF amplifier with a phase difference of 90 degrees, thereby generating in an empty coil a circularly polarized RF field. This is often referred to as quadrature drive.

As RF source the above-mentioned elements may be chosen and combined as desired. For example, for two channels used for generating a circularly polarized RF field in an empty coil, either two RF amplifiers providing RF signals that are phase shifted by 90 degrees may be used, or a quadrature hybrid that has the two phase shifted outputs and that is fed by a single RF amplifier.

A 'socket' is the socket of the RF coil which provides the connection point to the cables of the RF amplifier used to drive the RF coil. Thus, the RF coil is a single unit, the RF amplifier is a single unit, and these two units are to be connected by cables for providing the RF power, wherein these cables are plugged into the sockets. Typically, the sockets are provided as connectors which permit the cables to be connected via bayonet connectors or union nuts.

A 'first transmission line' comprises the entire electrical signal path from a socket to the associated coil element. Thus, the first transmission line may comprise any electrical connection between spatially distant locations 'socket' and 'coil element', that may be realized by any sequential combination of match and transmission lines (e.g. coaxial lines) and lumped element phase shifter circuitry, and that may be described by an electrical length psi as measured at the Larmor frequency of the respective MRI system. The lumped element phase shifters can be located at the beginning, somewhere in between, or at the end of the first transmission line. The matching circuit is typically located at the side of the first transmission line immediately facing the respective coil element.

Embodiments may have the advantage that an RF coil may be provided that can be electrically connected to respective RF sources in a simple manner: since the differences in electrical length between any differences in electrical length between any of the transmission lines is $k\lambda/4$, all points of connection 'sockets' to which the RF power is to be fed for driving the coil have a well-defined phase relationship. Thus, a set of standardized equal-electrical-length cables may be used from the RF source to the respective sockets to provide the RF power without the necessity to additionally perform any phase adjustments regarding the lengths of the cables due to an arbitrary phase relationship regarding the sockets. Any subsequent cumbersome adjustment of phases at the sockets after manufacturing of the RF coil is not required any more.

The term 'electrical length' refers to the length of an electrical conductor in terms of the phase shift introduced by transmission over that conductor at a given frequency f ($\lambda = v/f$ with f being the frequency and v the phase speed).

It has to be noted here that in case of a two channel MR coil the points of attachment of the first transmission lines to the respective coil elements may be intuitively chosen by a manufacturer in a symmetric manner such that the length of the respective two first transmission lines are identical. However, in case of a four or more channel MR coil, especially an RF body coil, a symmetric selection of the points of attachment of the first transmission lines to the respective coil elements is not possible any more. Here, the described adjustment of the difference in lengths between each of the transmission lines to $k\lambda/4$ nevertheless permits using a well-defined phase relationship of the RF signals for driving the coils.

It further has to be noted that the requirement of having the differences in electrical length between any differences in electrical length between any of the transmission lines set to $k\lambda/4$ is for a given wavelength $\lambda$ of an RF signal. Typically, that should be the wavelength corresponding to the frequency at which the coil is driven. In case the coil is driven at multiple frequencies, typically these frequencies are only a few hundred kHz in difference, such that as guiding value the average frequency value may be used for selecting $\lambda$.

In accordance with an embodiment of the invention, the RF coil has four channels with two pairs of the first transmission lines, wherein within each pair the first transmission lines are of the same electrical length and wherein the differences in electrical length between the first transmission lines of the two pairs is $\lambda/4$.

In accordance with an embodiment of the invention, k is an integer multiple of 4. This means that with respect to a set of RF signals with given phase relationship between all the RF signals and which is provided to the sockets, the respective coil elements associated to said sockets experience exactly the same phase relationship in an unmodified manner. Therefore, in case the RF sources are able to output the RF power or RF signals with the desired phase differences in between them, it would be sufficient to use a set of identical cables (identical in electrical length) to connect the outputs with the respective sockets—the length of the cable should not play any role here since in case identical cables are used for all sockets the phase relationship of the RF power provided by the RF sources is maintained at the sockets.

In accordance with an embodiment of the invention, each first transmission line is comprising an impedance matching network and a first phase shifting circuit directly attached (electrically connected) to the impedance matching network, wherein for each first transmission line the respective first phase shifting circuit is adapted for providing a compensation of the length of the respective first transmission line as determined in between its socket and its first phase shifting circuit such that said differences in electrical length between any differences in electrical length between any of the first transmission lines is $k\lambda/4$.

Generally, the purpose of an impedance matching network is to allow an adjustment such that the impedance of each coil element matches that of the respective RF source, typically 50Ω. By integrating the first phase shifting circuit to the impedance matching network, the location of length compensation regarding the differences in electrical length between any differences in electrical length between any of the transmission lines to $k\lambda/4$ is moved away from any wires located in between the socket and the impedance matching network. This may facilitate shielding of the coil from undesired electromagnetic waves (sheath current) emanating from the first transmission lines since these lines can be kept as short as possible while any length compensation, i.e. elongation of the first transmission lines is moved and concentrated onto the impedance matching network which can be well shielded from the interior of the coil.

In accordance with an embodiment of the invention, the first phase shifting circuit is anyone of a second transmission line and a lumped element phase shifter. Further, it may be possible that the first phase shifting circuit comprises elements that permit to fine-tune the input phases at each socket. The second transmission line may be a coaxial cable of predefined electrical length or any other cable that is able to extend the electrical signal path by a certain electrical length.

Preferably, the impedance matching network is immediately connected to the respective coil element. This may have the advantage that no free cables are required in between the impedance matching network and the respective coil element which again could be a source of undesired electromagnetic waves emanating from the first transmission line.

In accordance with an embodiment of the invention, the sockets are integrated in a housing of the RF coil. The coil may further comprise a terminal board comprising the sockets, wherein the terminal board is integrated in the housing of the RF coil. This may have the advantage that an out-of-the-box coil may be provided which can be easily installed in an MRI system, since the electrical connections from the RF sources to the coil for driving the coil can be realized by using e.g. cables of identical arbitrary length that are simply plugged into the available sockets in the housing of the coil.

In accordance with an embodiment of the invention, each first transmission line is comprising a second phase shifting circuit and a socket connector, the socket connector electrically connecting the respective coil element with its socket, each second phase shifting circuit electrically connecting the respective socket connector to the respective socket, wherein for each first transmission line the respective second phase shifting circuit is adapted for providing a compensation of the length of the respective first transmission line as determined in between its coil element and its socket connector such that said differences in electrical length between any differences in electrical length between any of the first transmission lines is $k\lambda/4$, wherein the second phase shifting circuits and the socket connectors are mounted to the terminal board or the housing of the RF coil.

This may have a similar advantage as discussed above regarding the first phase shifting circuit: by integrating the second phase shifting circuit towards the housing of the coil, preferably to the terminal board, the location of length compensation regarding the differences in electrical length between any differences in electrical length between any of the transmission lines to $k\lambda/4$ is moved away from any wires located inside the housing, where the respective wires of the first transmission line used to supply the RF power to the coil elements can be kept as short as possible. Again, this may facilitate shielding of the coil from undesired magnetic fields (jacket waves) emanating from the first transmission lines since these lines can be kept as short as possible while any length compensation, i.e. elongation of the first transmission lines is moved and concentrated to the terminal board which can be well shielded from the interior of the coil.

Similarly, as for the first phase shifting circuit, the second phase shifting circuit may be anyone of a further transmission line and a lumped element phase shifter. The second or further transmission line may be realized as a delay line, like a stripline or a coaxial cable.

In accordance with an embodiment of the invention, each first transmission line comprises a ground wire, wherein all the ground wires of all the first transmission lines are connected to a common ground at the terminal board. A capacitor may be placed in the ground cable to prevent induced eddy currents from the gradient field. This may further help to minimize irradiation of magnetic fields and reduce cable currents on the shield of the transmission lines and improves isolation between external connected feeding lines and coil. Further the influence of cross-coupling of individual coil ports is reduced and orthogonality of the coil is preserved.

In accordance with an embodiment of the invention, the coil is an RF body coil.

In another aspect the invention relates to a magnetic resonance imaging system for acquiring magnetic resonance data, the magnetic resonance system comprising:
 a main magnet for generating a main magnetic field within an imaging zone,
 a multi-channel magnetic resonance imaging RF coil with at least four channels, the RF coil being adapted for picking up magnetic resonance signals from the imaging zone, the RF coil comprising a coil element for each of the channels, the RF coil further comprising for each coil element a socket that is electrically coupled to said coil element via a respective first transmission line, each socket being adapted for receiving a plug for providing an RF signal via the respective first transmission line to the respective coil element, wherein with respect to a predefined RF signal the differences in electrical length between any differences in electrical length between any of the transmission lines is $k\lambda/4$ where k is an integer and $\lambda$ is the wavelength of the RF signal,
 associated to each channel an RF source for supplying radio-frequency power to the RF coil via the socket associated to the respective channel for driving the RF coil.

In accordance with an embodiment, the RF source is comprising for the supplying of the RF power a connection point, the system further comprising a cable for each RF source, the cable electrically connecting the respective connection point of the RF source with the socket associated to the RF source, the cable having a plug for being received by the respective socket, wherein with regard to the wavelength all the cables electrically connecting the connection points of the RF sources with the sockets have a differences in electrical length between any differences in electrical length between any other that is $n\lambda/4$ where n is an integer, preferably have the same electrical length (n=0). Preferably, the cables are identical in geometrical length.

In another aspect, the invention relates to method of servicing a magnetic resonance imaging system for acquiring magnetic resonance data, the magnetic resonance system comprising:
 a main magnet for generating a main magnetic field within an imaging zone,
 a multi-channel magnetic resonance imaging RF coil with at least four channels, the RF coil being adapted for picking up magnetic resonance signals from the imaging zone, the RF coil comprising a coil element for each of the channels, the RF coil further comprising for each coil element a socket that is electrically coupled to said coil element via a respective first transmission line, each socket being adapted for receiving a plug for providing an RF signal via the respective first transmission line to the respective coil element, wherein with respect to a predefined RF signal the differences in electrical length between any differences in electrical length between any of the transmission lines is $k\lambda/4$ where k is an integer and $\lambda$ is the wavelength of the RF signal,
 associated to each channel an RF source for supplying radio-frequency power to the RF coil via the socket associated to the respective channel for driving the RF coil,
 the method comprising electrically connecting all RF sources to the respective sockets with electrical cables, wherein with regard to the wavelength all the cables have a differences in electrical length between any other that is $n\lambda/4$ where n is an integer, preferably have the same electrical length.

This may be beneficial in that the servicing of an MRI system is simplified. There may be no necessity any more to measure electrical cables and driving ports of the RF coil in order to ensure choosing of a correct individual length of electrical cables that are used to feed RF power to the driving ports of the RF coil. Instead, in the example of a four channel RF coil four electrically identical cables may be used in order to electrically connect the RF sources to the respective coil elements via the sockets.

It is understood that one or more of the aforementioned embodiments of the invention may be combined as long as the combined embodiments are not mutually exclusive.

As will be appreciated by one skilled in the art, examples discussed in this disclosure may be embodied as an apparatus, method or computer program product. Accordingly, aspects may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage may be any volatile or non-volatile computer-readable storage medium.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the C programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects are described with reference to flow charts, block diagrams of methods, apparatus (systems) and computer program products. It is understood that each block or a portion of the blocks of the flowcharts, illustrations, and/or block diagrams, may be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks. A 'user interface' as used herein is an interface which allows a user or operator to interact with a computer or computer system.

A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) display, Electroluminescent display (ELD), Plasma display panel (PDP), Liquid crystal display (LCD), Organic light-emitting diode display (OLED), a projector, and Head-mounted display.

Magnetic Resonance (MR) data is defined herein as being the recorded measurements of radio frequency signals emitted by atomic spins using the antenna of a magnetic resonance apparatus during a magnetic resonance imaging scan. Magnetic resonance data is an example of medical imaging data. A Magnetic Resonance (MR) image is defined herein as being the reconstructed two or three dimensional visualization of anatomic data contained within the magnetic resonance imaging data.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

In the following, like numbered elements in the figures are either similar elements or perform an equivalent function. Elements which have been discussed previously will not necessarily be discussed in later figures if the function is equivalent.

Figure 1:
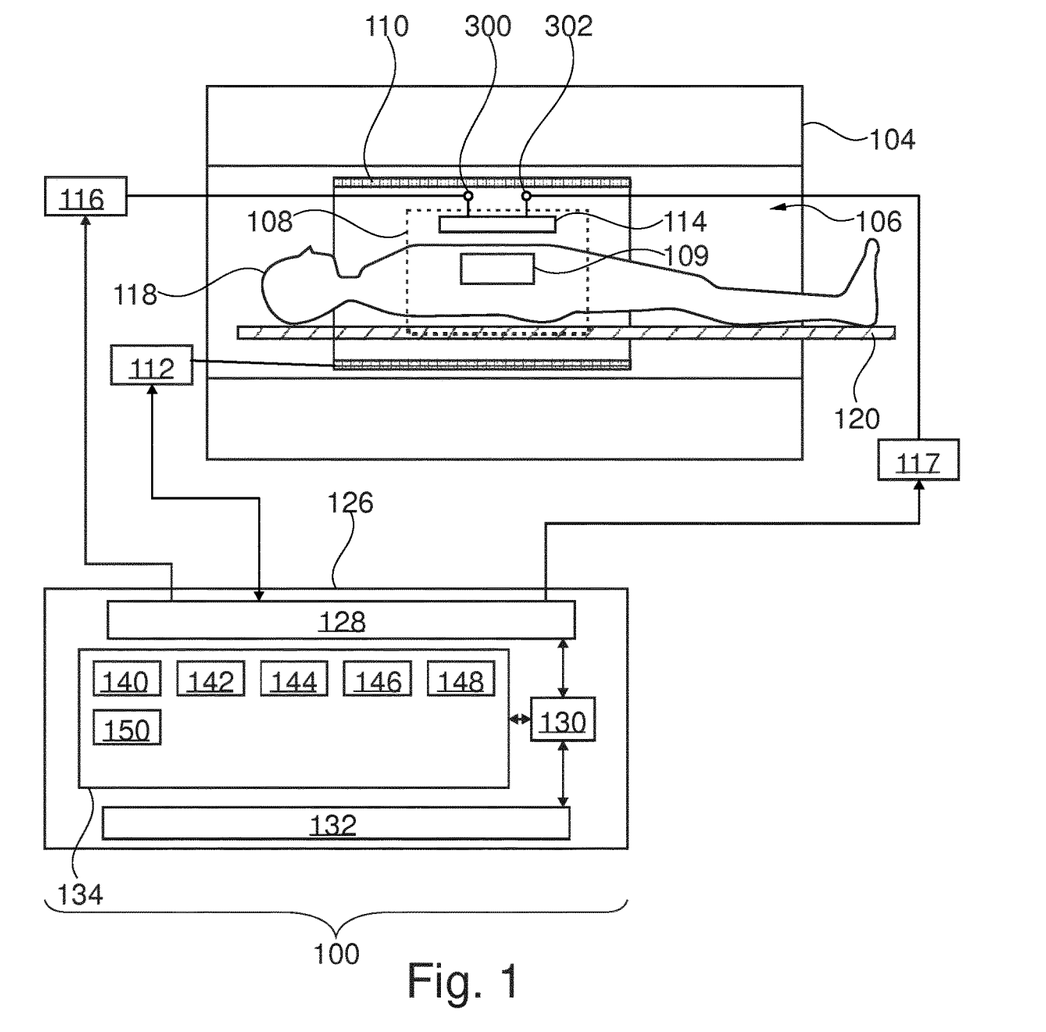
FIG. 1 illustrates an example of a magnetic resonance imaging system.

FIG. 1 shows an example of a magnetic resonance imaging system 100 with a magnet 104. The magnet 104 is a superconducting cylindrical type magnet with a bore 106 through it. The use of different types of magnets is also possible; for instance, it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 106 of the cylindrical magnet 104 there is an imaging zone 108 where the magnetic field is strong and uniform enough to perform magnetic resonance imaging. A region of interest 109 is shown within the imaging zone 108. A subject 118, for example a patient, is shown as being supported by a subject support 120, for example a moveable table, such that at least a portion of the subject 118 is within the imaging zone 108 and the region of interest 109.

Within the bore 106 of the magnet there is also a set of magnetic field gradient coils 110 which is used for acquisition of magnetic resonance data to spatially encode magnetic spins within the imaging zone 108 of the magnet 104. The magnetic field gradient coils 110 connected to a magnetic field gradient coil power supply 112. The magnetic field gradient coils 110 are intended to be representative. Typically, magnetic field gradient coils 110 contain three separate sets of coils for spatially encoding in three orthogonal spatial directions. A magnetic field gradient power supply supplies current to the magnetic field gradient coils. The current supplied to the magnetic field gradient coils 110 is controlled as a function of time and may be ramped or pulsed.

Adjacent to the imaging zone 108 is a radio-frequency coil 114 "RF antenna" for manipulating the orientations of magnetic spins within the imaging zone 108 and for receiving radio transmissions from spins also within the imaging zone 108. The radio frequency antenna contains multiple coil elements. The RF coil 114 has multiple sockets 300 and 302, wherein each socket corresponds to one antenna element. The radio-frequency coil 114 is connected via the socket 300 to an RF amplifier 116 and via the socket 302 to an RF amplifier 117. The radio frequency amplifiers 116 and 117 are providing RF power to the RF coil 114 with a phase difference of 90° for manipulating the orientations of magnetic spins within the imaging zone 108. The phase difference of 90° leads to generating in the coil 114 a circularly polarized RF field.

Instead of two RF amplifiers 116 and 117 a single RF amplifier may be used that has an RF output fed into a hybrid power splitter that serves to delay the phase of the signal to one of the sockets 300 and 302 by 90 degrees, thereby also generating in the coil the circularly polarized RF field.

The amplifier 116, the gradient controller 112 and the RF output terminal 302 are shown as being connected to a hardware interface 128 of a computer system 126. Thus, the computer system 126 serves also as receiver for receiving and processing the MR signals acquired using the coil 114.

The computer system further comprises a processor 130 that is in communication with the hardware system 128, a memory 134, and a user interface 132. The memory 134 may be any combination of memory which is accessible to the processor 130. This may include such things as main memory, cached memory, and also non-volatile memory such as flash RAM, hard drives, or other storage devices. In some examples the memory 130 may be considered to be a non-transitory computer-readable medium.

The computer memory 134 is shown as containing machine-executable instructions 140. The machine-executable instructions contain commands or instructions which enable the processor 130 to control the operation and function of the magnetic resonance imaging system 100. The computer memory 134 is shown as further containing imaging scan protocols 142. Each imaging scan protocol may comprise pulse sequence commands for one or multiple pulse sequences which are either instructions or data which may be converted into instructions which enable the processor 130 to control the magnetic resonance imaging system 100 to acquire magnetic resonance data. The pulse sequence commands may therefore be part of an imaging scan protocol. The magnetic resonance data may for instance be used to cause the magnetic resonance imaging system to perform multiple pulse repetitions which cause magnetic resonance signals 144 to be acquired. Each pulse corresponds to the supplying of RF power to the coil 114 by one of the RF amplifiers 116 and 117.

Magnetic resonance signals 144 are shown as being stored in the computer memory 134. The magnetic resonance signals 144 for a particular pulse repetition may be collated into the magnetic resonance data 146. The magnetic resonance data 146 may be used to generate a series of images 148. The imaging scan protocols may further comprise instructions 150 regarding the reconstruction of the image data 146 acquired using the imaging.

For example, the antenna 114 has multiple coil elements in a birdcage configuration. Further, multiple ones of the sockets 300 and 302 are provided which are coupled via respective transmission lines to respective ones of the coil elements. Similarly, multiple ones of RF amplifiers 116 and 117 may be provided.

Figure 2:
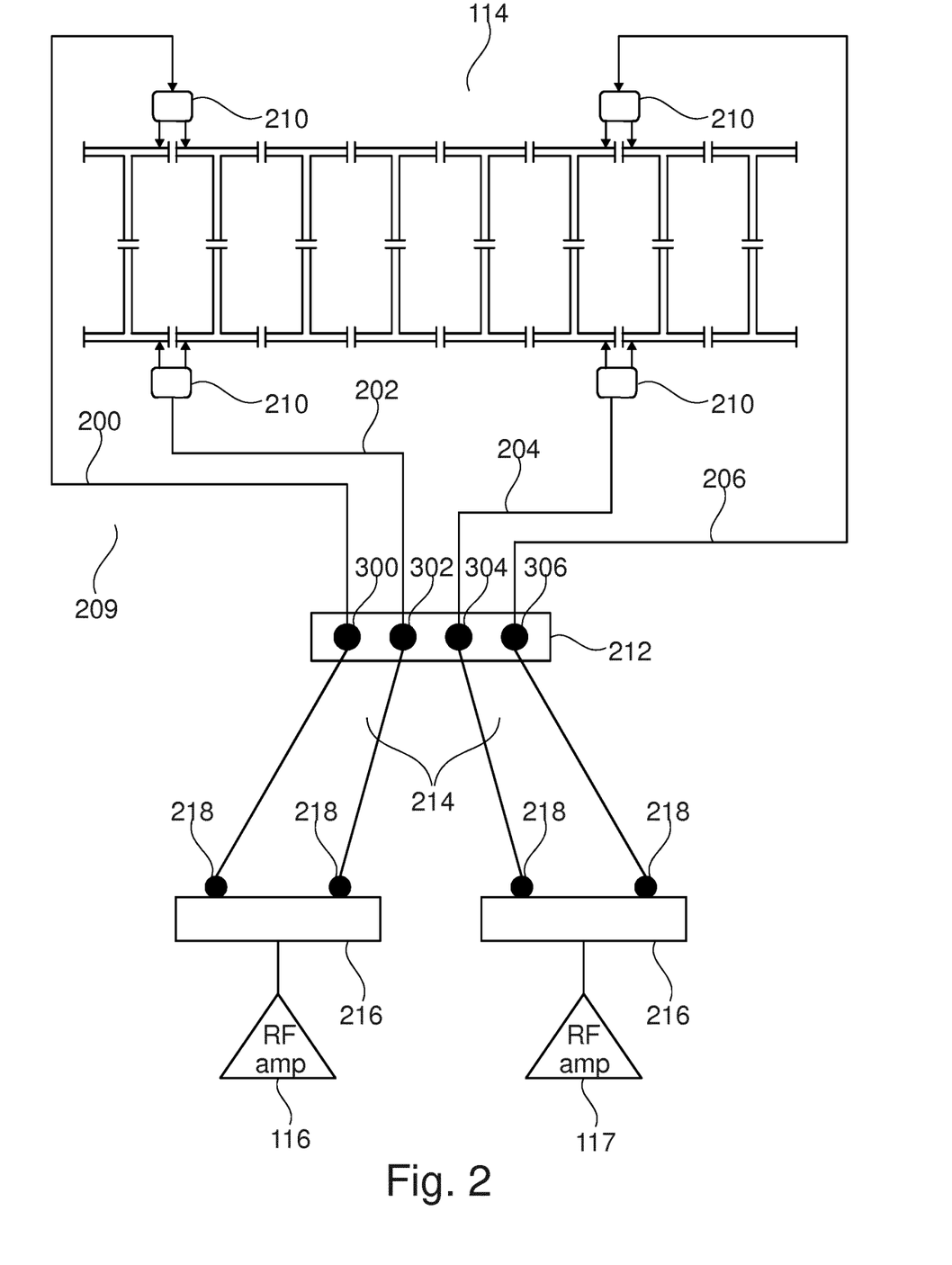
FIG. 2 is a circuit diagram of a birdcage resonator connected to various power sources.

FIG. 2 depicts the coil 114 and the connection setup with the amplifiers 116 and 117 in more detail. The coil 114 is for example a birdcage resonator. Typically, a birdcage coil consists of two circular conductive loops referred to as end rings connected by a number of conductive straight elements called rungs. In FIG. 2, the end rings are constituted by the horizontal conductor lines, whereas the rungs are constituted by the vertical conductor lines. Several capacitors are arranged between the individual conducting elements based on the frequency characteristics of the coil 114 desired. In total, the antenna 114 therefore consists of multiple coil elements that can be used for exciting nuclear spins by supplying RF pulses to the coil elements and to receive magnetic resonance signals also using the individual coil elements.

For each coil element a respective matching board 210 is provided which is immediately connected to the respective coil element. In more detail, each matching board comprises an 'impedance matching network' that is coupled to two conductive elements of each ring, wherein these two conductive elements are coupled to each other via a respective capacitor 310. Thus, a coil element can be understood as a single electrical conductor slab of the coil or an arrangement of electrical conductors slabs and optional capacitors that form a coil as part of the antenna. The purpose of the impedance matching network and thus the matching board 210 is to allow an adjustment such that the impedance of each coil element matches that of the respective RF source, typically 50Ω.

Each coil element is electrically coupled to a socket via a first transmission line. In FIG. 2 socket 300 is coupled to one of the coil elements of coil 114 via a transmission 209 line that comprises a cable 200 and a respective matching board 210. Similarly socket 302 is coupled to one of the coil elements of coil 114 via a transmission line that comprises a cable 202 and a respective matching board 210, socket 304 is coupled to one of the coil elements of coil 114 via a transmission line that comprises a cable 204 and a respective matching board 210 and socket 306 is coupled to one of the coil elements of coil 114 via a transmission line that comprises a cable 206 and a respective matching board 210. Typically, the cables 200-206 will be coaxial cables that are well shielded against the coil 114.

It has to be noted that the connection points of the transmission lines and the coil elements are only depicted schematically in FIG. 2. In practice the skilled person will choose the location of the connection points in such a manner that magnetic fields are generated in a desired manner.

A terminal board 212 is carrying all the sockets 300-306. On the terminal board 212 all the wires 200-206 are combined to a common ground. Typically, the coil 114 will be comprised in a housing and the terminal board 212 will be integrated into that housing in such a manner that the sockets 300-306 are accessible from outside the area that is surrounded by the body coil 114.

Figure 3:
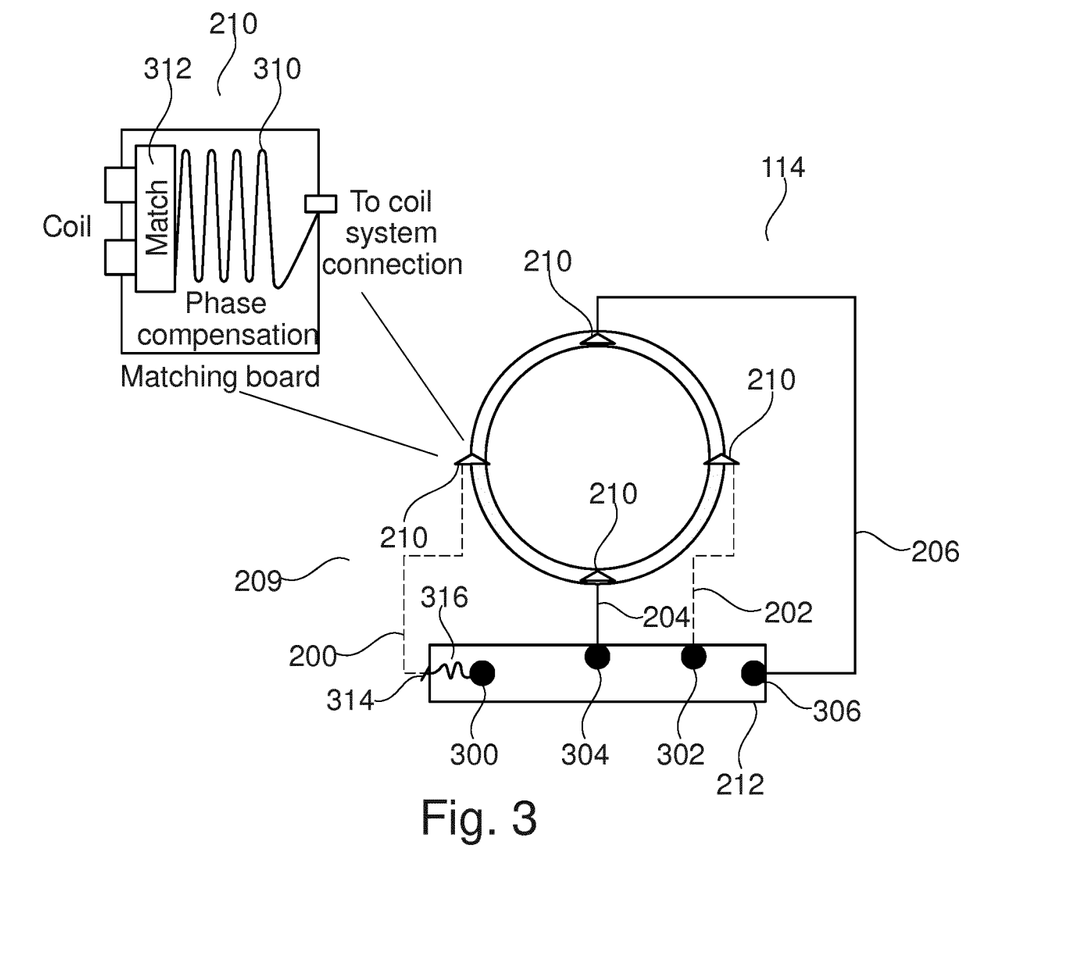
FIG. 3 is another circuit diagram of a birdcage resonator.

Each socket 300-306 is electrically coupled via a respective cable 214 with a connection point 218 that is provided by a respective RF source. In the example of FIG. 3 the RF sources are given by the outputs of quadrature hybrid power splitters 216. Each quadrature hybrid receives as input an RF signal from a respective RF source 116 and 117 and provides as output at the connection points 218 the RF signal with a respective phase 0° and 90°. Both RF amplifiers could be driven by the same RF input signal such that at the connection points 218 all the output RF signals have a predefined phase relationship.

In the following, it is assumed that the cables 214 are identical in electrical length. That means the RF signals of given wavelength output by the quadrature hybrids 216 experience during traveling through all cables the same phase shift. As a result, the phase relationship between the RF signals is the same for all the connection points 218 and the same for all the sockets 300-306.

The RF coil 114 is designed such that this phase relationship is maintained when then RF signal is provided to the coil elements. This is a special example in which the differences in electrical length between any of the first transmission lines is λ/4. This means that after the RF signals have traveled through the respective first transmission lines comprising the cables 200-206 and the matching boards 210 they still have the same phase relationship with respect to each other. As a result, all coil elements driven by the RF signals are driven with signals of a phase relationship that is predefined only by the RF sources themselves. One could consider the connection points 218 in a certain manner as the RF sources since these are the sources at which the RF signals are provided with their desired phase relationship.

As a consequence, it is fairly easy to setup a wiring of the body coil 114 with the respective RF sources since any of the cables 214 does not have to be designed in length specifically for the coil 114. In case the first transmission lines would be of different electrical length in an arbitrary manner, the phase relationship shown in FIG. 2 with respect to the connection points 218 (0°, 90°, 0°, 90°) would not hold any more. In this case one would have to determine the RF signal phase behavior for each first transmission line and then individually adapt the length of each of the cables 214 in order to compensate for undesired phase changes. In a practical example, in case an RF signal of phase 0° at the sockets 300 and 302 and traveling via the first transmission lines comprising the cables 200 and 202 would experience a phase at the respective coil elements of 75° and 85°, respectively, this would mean that the first transmission line involving the cable 202 is somehow electrically longer than the first transmission line involving the cable 200. Assuming a usually fixed phase relationship of 90° at the quadrature hybrids 216, a compensation for this phase difference of 10° could be achieved by appropriately changing the electrical length of one of the cables 214 connecting to the sockets 300 and 302.

Therefore, by means of the coil design discussed above, it is fairly easy to setup a wiring of the body coil 114 with the respective RF sources. It has to be noted that it is of course possible to use a different configuration of predefined phase relationships at the sockets 300-306: for example, the lengths of the first transmission lines comprising the cables 200-206 could be set in such a manner that with respect to a predefined RF signal the differences in electrical length between any of the transmission lines is $k\lambda/4$ where k is an integer and $\lambda$ is the wavelength of the RF signal. In a practical example, taking one of first transmission lines as reference 0° and assuming RF signals input to all of the sockets with a given phase relationship of 0° between any of the input RF signals, then the phase relationships of these RF signals at the coil elements could be predefined to −90°, 0°, −90°, −180° (in the order of sockets 300-306).

It has to be noted that in FIG. 2 not shown is a pre-amplifier and detune circuit to actively or passively blank a pre-amplifier during providing the RF power to the coil elements. Further not shown in FIG. 2 is an analogue-to-digital converter which may be placed behind the pre-amplifier and which serves to digitize the pre-amplified MR signal. All these components may also be considered as being part of the respective first transmission paths.

FIG. 3 depicts another coil 114. Again, the coil is a four-channel body coil which has four coil elements. Each coil element is electrically coupled via a first transmission line with a respective socket 300-306, the sockets being located on a terminal board 212. This is similar as discussed before with respect to FIG. 2. However, again it has to be noted that the connection points of the transmission lines and the coil elements are only depicted schematically in FIG. 3. In practice the skilled person will choose the location of the connection points in such a manner that magnetic fields are generated in a desired manner.

Each first transmission path comprises a respective cable 200-206 and one of the matching boards 210, which is shown in more detail in an enlarged version in FIG. 3. The matching board 210 has one terminal 'to coil system connection' to which the respective cable 200-206 is to be connected. The matching board 210 has two further terminals 'Coil' which are to be directly and immediately coupled to the coil element, i.e. coupled to two conductive elements of the respective ring constituting the coil element (also compare here FIG. 2). The matching board 210 comprises a matching circuit 312 which is the part of the board that allows for the adjustment such that the impedance of the respective coil element matches that of the respective RF source, typically 50Ω.

The matching circuit 312 and the terminal 'to coil system connection' are electrically coupled via phase shifting circuit, which in FIG. 3 is given by a second transmission line 'delay line' 310. The second transmission line 310 elongates the electrical path the RF signal has to travel. As a consequence, the second transmission line leads to a shifting of the phase of the RF signal when the signal arrives at the matching circuit 312.

Since the coil is provided in such a manner that with regard to a RF signal at a given phase input at the sockets 300-306 all coil elements experience this RF signal with the same phase shift or a phase shift in increments of 90°, the requirement is that with respect to the predefined RF signal the differences in electrical length between any of the transmission lines is $k\lambda/4$ where k is an integer and $\lambda$ is the wavelength of the RF signal. In order to elongate parts of the first transmission lines in order to achieve this goal, the second transmission lines 310 are provided in exact the desired length as needed: for each first transmission line the respective phase shifting circuit (here the length of the second transmission line 310) is adapted for providing a compensation of the length of the respective first transmission line as determined in between its socket 300-306 and its first phase shifting circuit 312 such that said differences in electrical length between any of the first transmission lines is $k\lambda/4$.

Of course, here it is assumed that the impedance matching network and their coupling to the respective coil element is the same for all first transmission lines such that any phase shifts induced by the impedance matching network and their coupling to the respective coil element are identical for all coil elements.

Another additional or alternative possibility to provide such a compensation of the length of the first transmission lines is given by another phase shifting circuit which is again realized in FIG. 3 as a third transmission line 316. The third transmission line 316 is coupling a socket connector 314 of the first transmission line 209 with the socket 300. For sake of simplification this principle of using the socket connector is only depicted in FIG. 3 for the socket 300. However, this can be extended in an analogous manner to all the other sockets and first transmission lines.

Again, in order to elongate parts of the first transmission lines in order to have a predefined RF signal relationship of phases, the third transmission lines 316 are provided in the desired length as needed: for each first transmission line the respective phase shifting circuit (here the length of the third transmission line 316) is adapted for providing a compensation of the length of the respective first transmission line as determined in between its socket connector 314 and the respective coil element such that said differences in electrical length between any of the first transmission lines is $k\lambda/4$.

In the following, the previously described idea is expressed in a more formal manner: an antenna 114 may comprise a number of N signal paths from the antenna ports (1 to N) to the terminal board 212. E.g. the transmission lines 200, 204, 202 and 206 may be described by psi2, psi3, psi4 and psi1. Psi(#i) denotes the electrical length of each signal path from the respective socket #i (300, 304, 302 and 306)

to each body coil port #i, i.e. each coil element. Psi(#i) is measured at the respective Larmor frequency of the MR system for which the body coil 114 is used. The differences between any of the length psi(i) are all k*λ/4 (k=integer).

An advantage may be that any cables external to the body coil, that must be externally handled and mounted on-site at the customer premises, can all have identical electric lengths. Further, the signals entering these external cables at the connection points 218 (see FIG. 2) can also have simple phase relations, i.e. their differences are expressible as m*λ/4 (m=integer).

A special case may be given by N=4, wherein Psi4=Psi3, Psi2=Psi1, Psi4-Psi1=λ/4.

Figure 4:
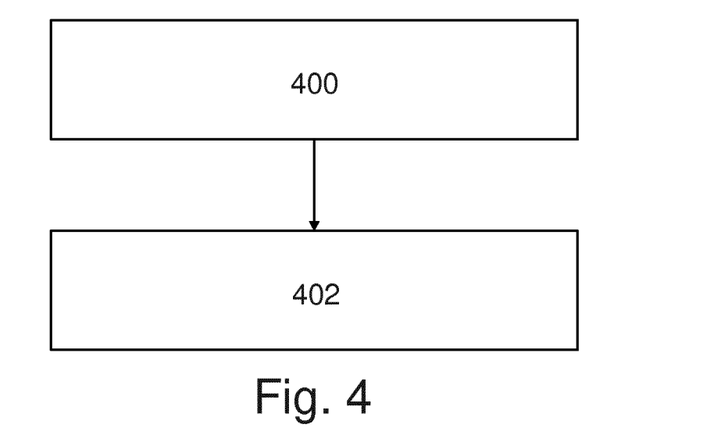
FIG. 4 is a flowchart illustrating a method of servicing a magnetic resonance imaging system, FIGS. 5a)-d) is a diagram of various body coils having different channels and arrangements of ports.

FIG. 4 is a flowchart of servicing a magnetic resonance imaging system for acquiring magnetic resonance data. The system may be the one shown in FIG. 1.

In step 400 all RF sources like the RF sources 218 of FIG. 2 are electrically connected to their respective sockets 300-306 with electrical cables, wherein with regard to an operating RF frequency of the MRI system all the cables have the same electrical length.

In step 402 the MRI system may be operated in a desired manner in order to acquire MR data.

Figure 5:
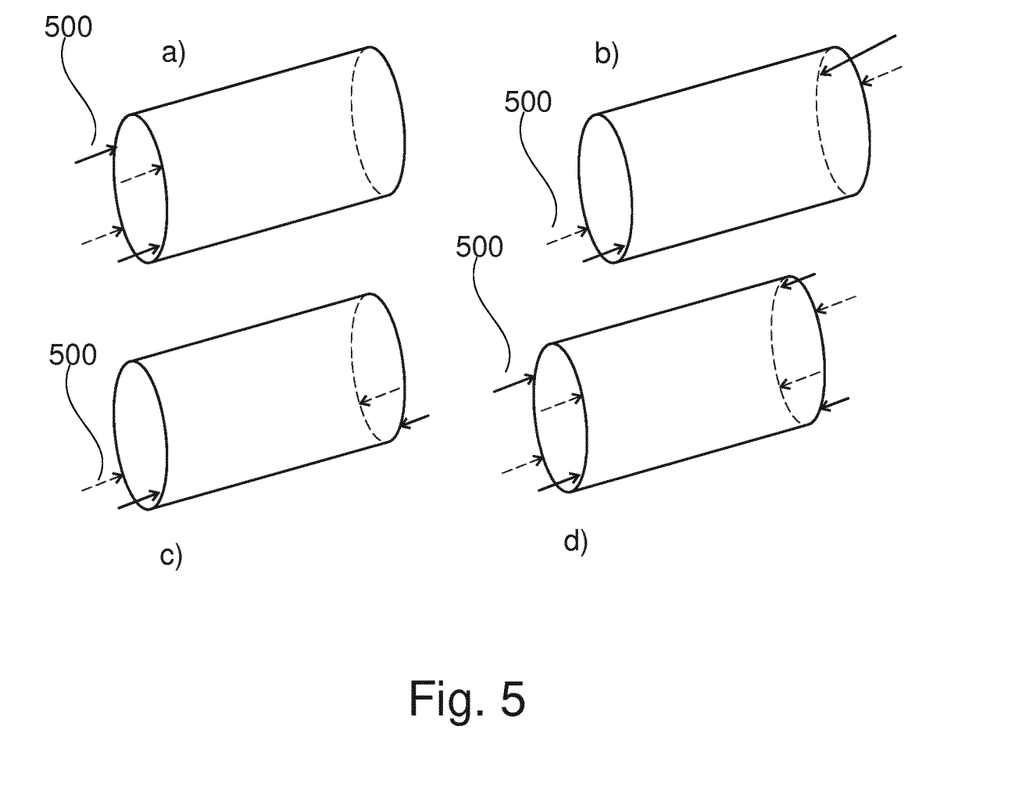

It should be pointed out, that there are several options in spatially allocating the ports, i.e. the connection points of the first transmission lines to the respective coil elements. Respective examples are shown in FIG. 5. FIGS. 5a, 5b and 5c show a body coil with 4 ports and two channels, wherein 2 ports 500 are each associated with a channel. The ports 500 are designated by an arrow, wherein ports belonging to a common channel are either designated by a solid or a dashed arrow. In FIG. 5a, the ports 500 are located on the same side (with respect to the distal end in longitudinal direction of the coil) of the coil. In FIG. 5b, the ports 500 are diagonally located on opposite sides of the coil and in FIG. 5c the ports 500 are located in a mirror symmetric manner on opposite sides of the coil. It has to be noted here that in case the ports are located on opposite sides of the coil (patient side, service side), it might be beneficial to have TWO terminal boards 212, i.e. one on each side.

In FIG. 5d, four ports 500 per channel are given as an example. Again, the ports 500 are designated by an arrow, wherein ports belonging to a common channel are either designated by a solid or a dashed arrow. The ports are arranged in a symmetric manner such that the arrangement of ports on one side of the coil corresponds to the arrangement of ports on the opposite side of the coil.

Generally, MRI requires a RF transmit chain of special type and performance: Pulse power capability in the order of 10 kW, within the order of 1 ms, short term high duty cycle RF pulses of about 100 ms, variable loading, superior linearity, stability, channel coupling in multi-channel TX systems, preferably non-magnetic components, preferably in strong static magnetic field and all that preferably with small costs.

A commercial RF chain at 3 Tesla utilizes 2 transmit channels. Typically the RF demand from individual channels is not equal in RF power and phase. At 1.5 Tesla the body coil is driven using a quadrature hybrid, thus only one amplifier is needed. The RF transmit chain at 3 T and 1.5 Tesla is under optimization regarding cost, B1 homogeneity, RF power requirements etc. A 4 port drive of the RF system volume body coil provides advantages regarding direct RF power combination in the coil and improved homogeneity. The coil can be driven using hardware hybrid combiners (Option for 1.5 Tesla) or directly using 4 RF amplifiers.

4 port feeding of a system volume body coil requires defined phase values of the individual ports. This makes the system more complex. 4-port-drive requires 0 90 180 270 degree phase shift for driving; external cable lengths need to be calibrated; a quadrature hybrid (QIB) can not be used, testing for quality check is difficult Disclosed is therefore a smart RF body coil, which has a defined system connection with fixed input phase parameters. For ease of use, a defined phase shift is directly integrated in the body coil. A fixed phase coil connection provides an interface for easy system connection and testing. RF quality testing and external cable management may therefore be are provided an easy to use concept. The coil can thus directly be connected to standard quadrature hybrids (QIB) or to RF amplifiers. External system cables may have equal lengths and external calibration is not required.

Described was a body coil with equal phase connection. The defined phase shift at the input ports of the body coil allows to connect directly 2 quadrature hybrids. No compensation of cable length at the external ports is required. Such an application is for a 1.5 Tesla new system RF chain.

Further described was a matching board for a body coil with fixed defined phase connection. The required phase shift is provided on the matching board using a coax cable or in combination with a lumped element phase shift combiner. Generally, the required phase shifts can be distributed over all the matching network of the coil, such that the required phase shift contributes from both matching boards. The defined phase shift at the input ports (sockets) of the body coil allows to connect directly 2 quadrature hybrids. No compensation of cable lengths at the external ports is required.

Further described was a body coil with equal phase connection. The defined phase shift at the input ports of the body coil allows connecting directly 4 RF power amplifiers, which can be driven with required phase shift without the need for compensation. An Application may be for a new system 3 T RF chain.

LIST OF REFERENCE NUMERALS 100 magnetic resonance imaging system
104 magnet
106 bore of magnet
108 imaging zone
109 region of interest
110 magnetic field gradient coils
112 magnetic field gradient coil power supply
114 radio-frequency coil
116 RF amplifier
117 RF amplifier
118 subject
120 subject support
126 computer system
128 hardware interface
130 processor
132 user interface
134 computer memory
140 machine-executable instructions
142 pulse sequence commands
144 magnetic resonance signals
146 magnetic resonance data
148 intermediate images
150 image reconstruction instructions
200 cable
202 cable 204 cable
206 cable
209 first transmission line
210 matching board
212 terminal board
214 cable
216 quadrature hybrid power splitter
218 connection point
300 socket
302 socket
304 socket
306 socket
310 second transmission line
312 matching circuit
314 socket connector
316 third transmission line
500 port

The invention claimed is:

1. A multi-channel magnetic resonance imaging radio frequency (RF) coil with at least four channels, the RF coil comprising:
a coil element for each of the channels; and
a socket corresponding to each coil element, wherein the socket is electrically coupled to said corresponding coil element via a respective first transmission line, each socket being adapted for receiving a plug for providing an RF signal via the respective first transmission line to the corresponding coil element, wherein with respect to a predefined RF signal differences in electrical length between any of the first transmission lines are $k\lambda/4$ resulting in a predefined phase relationship at the sockets, where k is an integer and $\lambda$ is the wavelength of the RF signal, the RF coil being configured to be driven at the wavelength of the RF signal,
wherein the RF coil has four channels with two pairs of the first transmission lines, wherein within each pair the first transmission lines are of the same electrical length as each other, and wherein the differences in electrical length between the first transmission lines of the two pairs is $\lambda/4$.

2. The coil of claim 1, wherein k is an integer multiple of 4.

3. The coil of claim 1, each first transmission line comprising an impedance matching network and a first phase shifting circuit directly attached to the impedance matching network, wherein for each first transmission line the respective first phase shifting circuit is adapted for providing a compensation of the length of the respective first transmission line as determined in between its socket and its first phase shifting circuit such that said differences in electrical length between any of the first transmission lines is $k\lambda/4$.

4. The coil of claim 3, the first phase shifting circuit being one of a second transmission line and a lumped element phase shifter.

5. The coil of claim 3, the impedance matching network being immediately connected to the corresponding coil element.

6. The coil of claim 1, the sockets being integrated in a housing of the RF coil.

7. The coil of claim 6, further comprising a terminal board, the terminal board comprising the sockets, the terminal board being integrated in the housing of the RF coil).

8. The coil of claim 7, each first transmission line comprising a ground wire, wherein all the ground wires of all the first transmission lines are connected to a common ground at the terminal board.

9. The coil of claim 3, each first transmission line comprising a second phase shifting circuit and a socket connector, the socket connector electrically connecting the corresponding coil element with its socket, each second phase shifting circuit electrically connecting the respective socket connector to the respective socket, wherein for each first transmission line the respective second phase shifting circuit is adapted for providing a compensation of the length of the respective first transmission line as determined in between its coil element and its socket connector such that said differences in electrical length between any of the first transmission lines is $k\lambda/4$, wherein the second phase shifting circuits and the socket connectors are mounted to the terminal board or the housing of the RF coil.

10. The coil of claim 1, the coil being an RF body coil.

11. A magnetic resonance imaging system for acquiring magnetic resonance data, the magnetic resonance system comprising:
a main magnet for generating a main magnetic field within an imaging zone,
the multi-channel magnetic resonance imaging RF coil of claim 1, and
associated to each channel an RF source for supplying radio-frequency power to the RF coil via the socket associated to the respective channel for driving the RF coil.

12. The system of claim 11, wherein each RF source comprises a respective connection point for the supplying of the RF power, the system further comprising a cable for each RF source, the cable electrically connecting the respective connection point of the RF source with the socket associated to the RF source, the cable having a plug for being received by the respective socket, wherein with regard to the wavelength all the cables electrically connecting the connection points of the RF sources with the sockets have differences in electrical length between any other cable of $n\lambda/4$, where n is an integer.

13. The system of claim 12, wherein n equals zero.

14. The system of claim 11, wherein k is an integer multiple of 4.

15. The system of claim 11, each first transmission line comprising an impedance matching network and a first phase shifting circuit directly attached to the impedance matching network, wherein for each first transmission line the respective first phase shifting circuit is adapted for providing a compensation of the length of the respective first transmission line as determined in between its socket and its first phase shifting circuit such that said differences in electrical length between any of the first transmission lines is $k\lambda/4$.

16. The system of claim 15, the first phase shifting circuit being one of a second transmission line and a lumped element phase shifter.

17. The system of claim 15, each first transmission line comprising a second phase shifting circuit and a socket connector, the socket connector electrically connecting the corresponding coil element with its socket, each second phase shifting circuit electrically connecting the respective socket connector to the respective socket, wherein for each first transmission line the respective second phase shifting circuit is adapted for providing a compensation of the length of the respective first transmission line as determined in between its coil element and its socket connector such that said differences in electrical length between any of the first transmission lines is $k\lambda/4$, wherein the second phase shifting circuits and the socket connectors are mounted to the terminal board or the housing of the RF coil.

18. A method of servicing a magnetic resonance imaging (MRI) system, the method comprising:

providing a multi-channel magnetic resonance imaging radio frequency (RF) coil, wherein the RF coil has at least four channels, the RF coil being adapted for picking up magnetic resonance signals from an imaging zone of the MRI system, the RF coil including a coil element for each of the channels a socket corresponding to each coil element, wherein the socket is electrically coupled to said corresponding coil element via a respective first transmission line, each socket being adapted for receiving a plug for providing an RF signal via the respective first transmission line to the corresponding coil element, wherein with respect to a predefined RF signal the differences in electrical length between any of the transmission lines are $k\lambda/4$, where k is an integer and $\lambda$ is the wavelength of the RF signal, the RF coil being configured to be driven at the wavelength of the RF signal, wherein the RF coil has four channels with two pairs of the first transmission lines, wherein within each pair the first transmission lines are of the same electrical length as each other, and wherein the differences in electrical length between the first transmission lines of the two pairs is $\lambda/4$, wherein the MRI system includes a plurality of RF sources, wherein the RF sources are each associated to an associated one of the channels for supplying radio-frequency power to the RF coil via the socket associated to the corresponding channel, for driving the RF coil, electrically connecting the RF sources to the respective sockets with electrical cables, wherein with regard to the wavelength all the cables have differences in electrical length between any other cable of $n\lambda/4$, where n is an integer resulting in a predefined phase relationship at the sockets; and acquiring magnetic resonance (MR) data by operating the MRI system in a prescribed manner to obtain data for servicing the MRI system.

19. The method of claim 18, wherein k is an integer multiple of 4.

20. The method of claim 18, each first transmission line comprising an impedance matching network and a first phase shifting circuit directly attached to the impedance matching network, wherein for each first transmission line the respective first phase shifting circuit is adapted for providing a compensation of the length of the respective first transmission line as determined in between its socket and its first phase shifting circuit such that said differences in electrical length between any of the first transmission lines is $k\lambda/4$.

* * * * *